United States Patent [19]

Schulman

[11] Patent Number: 5,503,822
[45] Date of Patent: Apr. 2, 1996

[54] MEDICATED GEL

[76] Inventor: Jerome M. Schulman, 4545 W. Touhy, Chicago, Ill. 60645

[21] Appl. No.: 221,775

[22] Filed: Apr. 1, 1994

[51] Int. Cl.$^6$ .............. A61K 7/22; A61K 7/26; A61K 35/78; A61K 9/06
[52] U.S. Cl. .............. 424/49; 424/54; 424/58; 424/195.1
[58] Field of Search ............... 424/191.1, 49–58

[56] References Cited

U.S. PATENT DOCUMENTS

| | | | |
|---|---|---|---|
| 3,923,984 | 12/1975 | Zuercher | 424/195 |
| 4,191,750 | 3/1980 | Hodosh | 424/127 |
| 4,283,421 | 8/1981 | Ray | 424/317 |
| 4,307,075 | 12/1981 | Martin | 424/28 |
| 4,350,785 | 9/1982 | Habib | 524/55 |
| 4,393,066 | 7/1983 | Garrett et al. | 424/251 |
| 4,405,610 | 9/1983 | Krnjevic | 424/180 |
| 4,466,956 | 8/1984 | Leeds | 424/80 |
| 4,585,656 | 4/1986 | Rosenthal et al. | 424/195.1 |
| 4,654,212 | 3/1987 | Hodosh | 424/127 |
| 4,708,873 | 11/1987 | Schulte | 424/195.1 |
| 4,725,438 | 2/1988 | Leazer | 424/195.1 |
| 4,748,022 | 5/1988 | Busciglio | 424/195.1 |
| 4,788,052 | 11/1988 | Ng et al. | 424/53 |
| 4,810,496 | 3/1989 | Jensen | 424/127 |
| 4,839,156 | 6/1989 | Ng et al. | 424/53 |
| 4,839,157 | 6/1989 | Ng et al. | 424/53 |
| 4,847,078 | 7/1989 | Sheppard et al. | 424/80 |
| 4,853,213 | 8/1989 | Thame | 424/58 |
| 5,081,157 | 1/1992 | Pomerantz | 514/781 |
| 5,081,158 | 1/1992 | Pomerantz | 514/781 |
| 5,100,653 | 3/1992 | Campo | 424/54 |
| 5,112,620 | 5/1992 | Repka et al. | 514/180 |
| 5,182,104 | 1/1993 | Marcus et al. | 424/78.07 |
| 5,198,217 | 3/1993 | Vedros | 424/195.1 |
| 5,266,318 | 11/1993 | Taylor-McCord | 424/195.1 |
| 5,294,434 | 3/1994 | King et al. | 424/58 |
| 5,294,440 | 3/1994 | Jack et al. | 424/78.05 |
| 5,324,746 | 6/1994 | McKee et al. | 514/330 |
| 5,362,737 | 11/1994 | Vora et al. | 514/291 |
| 5,378,465 | 1/1995 | Zeines | 424/195.1 |
| 5,409,703 | 4/1995 | McMalley et al. | 424/435 |
| 5,420,114 | 5/1995 | Clodman et al. | 512/23 |
| 5,420,114 | 5/1995 | Clodman et al. | 512/23 |
| 5,438,075 | 8/1995 | Skubitz et al. | 514/563 |

FOREIGN PATENT DOCUMENTS 2659462 7/1978 Germany.
2236760 4/1991 United Kingdom.

*Primary Examiner*—Shep K. Rose

[57] ABSTRACT

An improved tooth, gel or paste which includes silicon dioxide, aloe vera and allantoin which cures and prevents the formation of lesions and aphthous ulcers minor and other ailments on the oral mucosa.

9 Claims, No Drawings

MEDICATED GEL

BACKGROUND OF THE INVENTION

1. Field of the Invention

The invention relates in general to an improved medicated toothpaste in the form of a gel.

2. Description of Related Art

Aloe vera extract has been used in toothpaste as shown by U.S. Pat. No. 4,853,213. This patent also includes the use of a dried extract from the perennial herb periwinkle.

SUMMARY OF THE INVENTION

The present invention relates to a novel medicinal gel, which includes aloe vera, allantoin and silicon dioxide.

The compositions of the present invention can be applied to the oral mucosa with a cotton tip applicator or as a gel or as a mouth rinse and is effective for curing aphthous ulcers minor on the oral mucosa. The primary medicinal ingredients in the gel are aloe vera, allantoin and silicon dioxide, which may be combined in a gel or mouthwash and combined with other ingredients such as sodium fluoride in a dentifric base, sorbitol, water, hydrated silica, glycerin, sodium lauryl sulfate, cellulose gum, flavor, sodium saccharin, disodium phosphate and titanium dioxide.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

DETAILED DESCRIPTION OF THE PREFERRED EMBODIMENTS

The medicament may be in the form of a gel that contains aloe vera extract (of about 0.125%) which is derived from the Aloe Barbadensis Miller plant, allantoin (0.35%) which is a centrated gell and an abrasive material such as silicon dioxide.

Aloe vera is a white to tan powder that has been used in cosmetic basis and other products for use on the skin. Derivatives of this substance have been used in the treatment of burns, skin ulcers and as an antibacterial agent.

Allantoin was discovered by Vanquelin and Buniva in 1800 and was synthesized by Grimax in 1876. It is a white non-toxic, non-irritating and non-allergenic powder which decreases pain and promotes epithelial stimulation. Silicon dioxide was also combined in the mixture.

Studies were made with a number of patients using the medicant of the invention to demonstrate ulcer duration, intervals between lesions, size, pain and number of ulcers during the study.

A double blind study including forty-three subjects were used who had an average reoccurrence of aphthous ulcers at least twice every two months and had the presence of an ulcer at the time of the baseline examinations. The age range was 18–60 years and the subjects were in good health.

The diagnosis of aphthous ulcers was made based on 1) the history of recurring ulcers on the oral mucosa surfaces that were painful and healed without scarring; and 2) the clinical appearance and location of the distinct ulcers on their oral mucosa surface with a surrounding erythema, ragged borders and a yellow-white covering of the ulcer. After initial examination and demonstrating the method of the gel application to the subject, each subject was assigned to a group by random numbers and was given the medication for that group. The eight equal groups were the following:

Group 1: 5 subjects: control material, carrier gel without silicon dioxide, aloe or allantoin, Group 2: 5 subjects: silicon dioxide alone, Group 3: 5 subjects: aloe vera alone, Group 4: 5 subjects: allantoin alone, Group 5: 5 subjects: silicon dioxide and aloe vera, Group 6: 5 subjects: silicon dioxide and allantoin, Group 7: 5 subjects: aloe and allantoin, Group 8: 5 subjects: silicon dioxide, aloe vera, and allantoin.

The subjects applied the gel on the lesion using cotton swabs such as ("Q-Tip") and then brushed their teeth with a gel spreading it throughout the oral mucosa. The subjects did not rinse or eat for one-half hour after use. The subjects kept a personal diary to keep a record of the location, size, date and healing, size score, and level of pain caused by the lesion. The diary was used everyday that lesions were present. The subjects were seen weekly by investigators for the first month and then on a monthly basis for three months for a total of six visits.

Thirty-four subjects completed the entire three months of the study. The subjects that participated had a mean age of 35 years with a range of 19–56 years and there were twenty-four female and ten male subjects. The amount of gel used by the subjects during the three-month study varied from 146.7 to 256.4 grams. The mean duration of the lesions ranged from 6–11 days as shown in Table 1. Lesions of the control group lasted an average of nine days compared with subjects using allantoin alone, Group 4, silicon dioxide and allantoin Group 6, aloe vera alone Group 3 and silicon dioxide, allantoin and aloe vera, Group 8. Table 2 demonstrates a significant change in ulcer duration ($F=3.07$, $p=0.017$). The subjects using the gel with silicon dioxide, allantoin and aloe vera Group 8, had a significant reduction in lesion duration compared to the control gel Group 1 ($p=0.0360$). There were no other significant results in other groups compared to the control gel Group 1.

The results of the study indicated that a statistical important effect was generated with the gel when all three of the medicants silicon dioxide, aloe vera and allantoin were present.

TABLE 1

| GROUP | NO. | LM | IM | SM | PM | No/L |
| --- | --- | --- | --- | --- | --- | --- |
| Group 1 | 4 | 9.01 ± 1.32 | 3.53 ± 2.37 | 2.30 ± .40 | 1.80 ± .56 | .70 ± .51 |
| Group 2 | 4 | 10.20 ± 2.52 | 4.31 ± 8.93 | 1.81 ± 0.22 | 2.12 ± 14 | .78 ± .41 |
| Group 3 | 3 | 6.38 ± 0.73 | 23.70 ± 26.44 | 1.85 ± 0.33 | 1.90 ± .16 | .34 ± .22 |
| Group 4 | 4 | 7.32 ± 1.31 | 5.65 ± 6.11 | 1.95 ± 0.75 | 1.71 ± .52 | .75 ± .63 |
| Group 5 | 4 | 10.68 ± 3.31 | 6.77 ± 10.45 | 2.14 ± 0.18 | 2.21 ± .53 | .93 ± .82 |
| Group 6 | 5 | 6.41 ± 2.29 | 12.62 ± 16.06 | 2.30 ± 0.87 | 1.74 ± .54 | .39 ± .20 |

TABLE 1-continued

| GROUP | NO. | LM | IM | SM | PM | No/L |
|---|---|---|---|---|---|---|
| Group 7 | 5 | 9.43 ± 3.29 | 2.10 ± 7.12 | 1.86 ± 0.81 | 1.57 ± .96 | .81 ± .60 |
| Group 8 | 5 | 5.61 ± 1.49# | 4.57 ± 7.85 | 2.18 ± 0.83 | 1.86 ± .43 | .72 ± .68 |

Group 1: Control gel
Group 2: Silicon dioxide
Group 3: Aloe Vera
Group 4: Allantoin
Group 5: Silicon dioxide, Aloe vera
Group 6: Silicon dioxide, Allantoin
Group 7: Aloe vera, Allantoin
Group 8: Silicon dioxide, Aloe vera, Allantoin

TABLE 2

The results of analysis of variances for the data of dependent variables of the means for duration (LM), interval between lesions (IM), score for size of lesion (SM), score of pain from the lesion (PM), and ratio of sum duration of ulcers for the length of time of subjects, participation in the study (NO/L).

| Dependent Variable | Mean | F | P |
|---|---|---|---|
| LM | 8.10 | 3.07 | 0.017 |
| IM | 7.43 | 1.21 | 0.333 |
| SM | 2.06 | 0.42 | 0.884 |
| PM | 1.85 | 0.61 | 0.746 |
| NO/L | 0.68 | 0.55 | 0.785 |

Thus, toothpaste in the form of a gel which contains aloe vera, allantoin and silicon dioxide resulted in rapid healing of aphthous ulcers minor. Ranges of percentage of the ingredients are: aloe vera extract—0.05 to 2.5%, allantoin—0.5 to 1.0% and silicon dioxide—1 to 15%. The remaining ingredients were flavoring, glycerin, cellulose gum, saccharin and other inactive substances. The mixture is preferably formed into a gel although it may be a toothpaste or a mouthwash.

The composition may or may not include fluorine.

It is seen that toothpaste of this invention comprises an improved medicated gel or toothpaste which is valuable for healing ulcers in the mouth. Although it has been described with respect to preferred embodiments, it is not to be so limited as changes and modifications can be made therein which are within the full intended scope of the invention as defined by the appended claims.

I claim as my invention:

1. An oral hygiene method for healing oral ulcers, the method comprising the step of applying to the oral recurring apthous ulcers on the oral mucosa of subjects having a history of recurring aphthous ulcers a composition containing 0.05 to 2.5% by weight of aloe vera extract, 0.1 to 1.0% by weight of allantoin and 1 to 15% by weight of silicon dioxide until significant reduction in lesions are achieved, as well as more rapid healing, as compared to aloe vera and allantoin used alone on said recurring ulcers, or used together on said recurring ulcers.

2. The method of claim 1 wherein the composition is in the form of a gel.

3. The method of claim 1 wherein the composition is in the form of a tooth paste.

4. The method of claim 1 wherein the composition is in the form of a mouthwash.

5. The method of claim 1 wherein the composition includes sorbitol, glycerin, cellulose gum, flavoring, and saccharin.

6. The method of claim 1 wherein the aloe vera extract is about 0.1 to 0.2% by weight.

7. The method of claim 1 wherein the aloe vera extract is about 0.25% by weight.

8. The method of claim 1 wherein the allantoin is about 0.25 to 0.45% by weight.

9. The method of claim 1 wherein the silicon dioxide is about 5 to 10% by weight.

\* \* \* \* \*